United States Patent [19]

Ylvisaker

[11] Patent Number: 4,582,049

[45] Date of Patent: Apr. 15, 1986

[54] PATIENT INITIATED RESPONSE METHOD

[76] Inventor: Carl J. Ylvisaker, 11600 S. Barnes Rd. #110, Portland, Oreg. 97225

[21] Appl. No.: 531,256

[22] Filed: Sep. 12, 1983

[51] Int. Cl.⁴ .......................... A61H 29/00; A61N 1/00
[52] U.S. Cl. .................................. 128/24.1; 128/421; 128/423 W
[58] Field of Search ...................... 128/24.1, 905, 422, 128/80 G, 421, 423, 733, 419 PG; 623/24, 25

[56] References Cited

U.S. PATENT DOCUMENTS

| | | | |
|---|---|---|---|
| 3,628,538 | 12/1971 | Vincent | 128/422 |
| 3,641,993 | 2/1972 | Gaarder et al. | 128/733 |
| 3,905,355 | 9/1975 | Brudny | 128/905 X |
| 3,916,876 | 11/1975 | Freeman | 128/905 X |
| 4,165,750 | 8/1979 | Aleev et al. | 128/422 |
| 4,324,253 | 4/1982 | Greene et al. | 128/421 |
| 4,408,609 | 10/1983 | Axelgaard | 128/421 |
| 4,461,301 | 7/1984 | Ochs | 128/905 X |
| 4,480,830 | 11/1984 | Petrofsky et al. | 128/25 R X |

Primary Examiner—Richard J. Apley
Assistant Examiner—Kathleen D'Arrigo
Attorney, Agent, or Firm—Kolisch, Hartwell & Dickinson

[57] ABSTRACT

A patient-initiated response device and method for re-educating debilitated muscle tissue. The method comprises the detection of an electromyographic signal in a muscle group, which is used to trigger an artificial stimulation signal of a higher pre-determined intensity and transmit such a signal to a debilitated muscle group. The patient-initiated electromyographic signal may be detected in a debilitated or non-debilitated muscle group. The device detects an electromyographic signal of a pre-determined intensity and then generates and transmits an artificial stimulation signal to a muscle group at a frequency and intensity determined by the device operator.

4 Claims, 3 Drawing Figures

PATIENT INITIATED RESPONSE METHOD

BACKGROUND AND SUMMARY OF THE INVENTION

The present invention relates to an apparatus and the method for a re-education of a debilitated muscle group including the brain control which initiates and monitors the muscle groups activity. Specifically, the invention relates to an apparatus and method for re-educating a debilitated muscle group by means of a patient-initiated response device (PIRD) which detects an electromyographic (EMG) signal in a muscle group, which signal is voluntarily initiated by a patient undergoing treatment, and which, in response to the patient initiated signal, then transmits an artificial stimulation signal to a debilitated muscle group.

Muscle groups in the human body become debilitated in a variety of ways. One of the most common muscle debilitating events is a stroke. Muscle debilitation also occurs through nerve damage and some forms of nerve and/or muscle atrophy. Debilitated muscle groups can be restored to near normal functioning by re-educating the muscle to respond to nerve stimuli.

Debilitated muscle groups have been artifically stimulated by devices which transmit a stimulation impulse to the muscle group through an electrode inserted in a muscle group, or through an electrode placed on the patients skin adjacent a muscle group.

Artificial stimuli generation takes a variety of forms. One form is a computerized stimulation generator which produces stimulation impulses in a set pattern to produce movement of the patient's muscles. Another form involves the generation of an artificial stimulus by merely completing an electrical circuit, which is manually opened or closed, by either a physical therapist or the patient and includes a power source and some form of stimulation electrode. In some aspects, this type of device may be termed a patient-initiated response device, however, as the term is used in the instant application, it refers to a device which detects an electromyographic signal voluntarily initiated by the patient which acts as a triggering signal for a device which produces an artificial stimulation signal which is then transmitted to a debilitated muscle group.

An object of the instant invention is to provide a patient-initiated response device for the re-education of a debilitated muscle group.

Another object of the instant invention is to provide a PIRD which will detect an electromyographic signal in a debilitated muscle group, and transmit an artificial stimulation signal into the same debilitated muscle group.

A further object of the instant invention is to provide a PIRD which will detect an electromyographic signal in a muscle group and which will then transmit an artificial stimulation signal to a debilitated muscle group.

The present invention utilizes a transcutaneous electrode to detect an electromyographic signal in a muscle group, which may or may not be a debilitated muscle group. The detected signal is transmitted to a control device which analyzes the signal to determine if the signal exceeds a level set by an adjustable threshold detection circuit. If the level is exceeded, the circuitry generates and transmits an artificial stimulation signal to another transcutaneous electrode which is positioned adjacent a debilitated muscle group.

The device may be used, therefore, to detect a voluntary patient-initiated electromyographic signal in a muscle group, and then generate an artificial stimulation signal which is transmitted to a debilitated muscle group. In some instances, the patient-initiated signal and the artificial stimulation will affect the same muscle group. In other instances, the patient may initiate a voluntary signal in one muscle group, thereby artificially stimulating another muscle group.

These and other objects and advantages of the present invention will become more fully apparent as the description which follows is read in conjunction with the drawings.

DETAILED DESCRIPTION OF A PREFERRED EMBODIMENT

Figure 1:
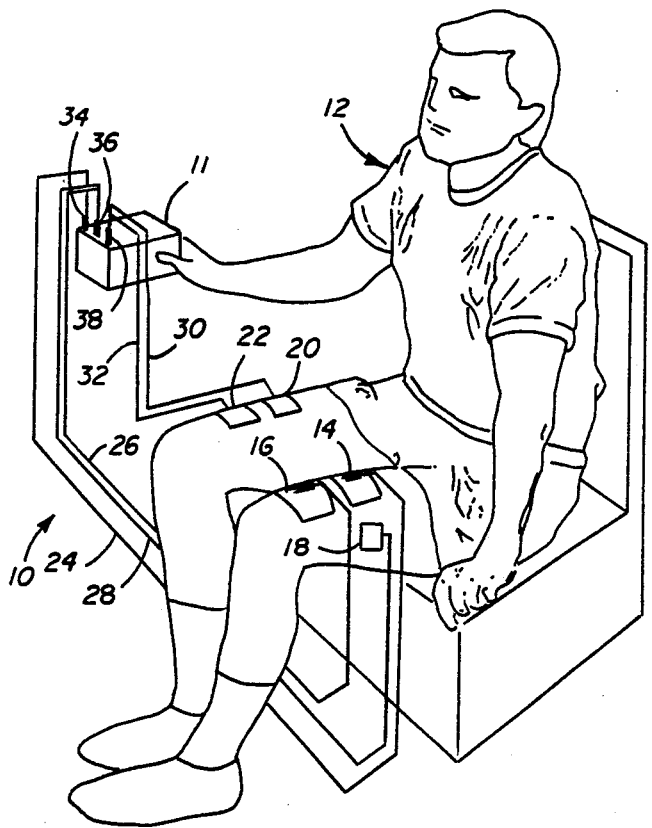
FIG. 1 depicts a patient utilizing a patient-initiated response device of the present invention.

Turning now to the drawings, and in particular to FIG. 1, a patient-initiated response device (PIRD) is depicted generally at 10. A patient undergoing treatment is depicted at 12. Patient 12 is connected to device 10 by means of a series of wire leads and a set of transcutaneous surface electrodes. An active electrode 14, a reference electrode 16 and a ground electrode 18 are positioned on the patient's left leg. Remote electrodes 20, 22 are positioned on the patient's right leg.

The electrodes are connected to control unit 11 by means of a series of shielded cables or leads. Active electrode 14 is connected by means of lead 24; reference electrode 16 by means of lead 26; ground electrode 18 by means of lead 28; and remote electrodes 20,22 by leads 30, 32 respectively.

Leads 24 through 32 may terminate at miniature phone jacks. Thus, lead 24 terminates at miniature phone jack 34. Lead 26 and lead 28 terminate at a common reference/ground jack 36. Leads 30, 32 terminate at a single remote jack 38.

Figure 2:
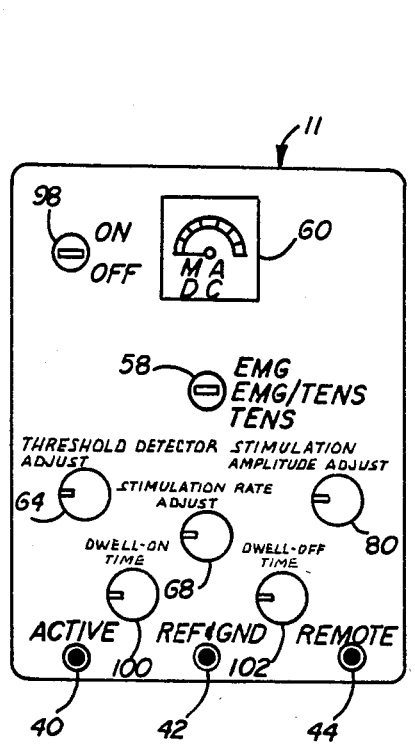
FIG. 2 is a top plan view of a control unit of the device of the present invention.

Turning now to FIG. 2, control unit 11 is shown in greater detail. Jack 34 is connected to control unit 11 by means of plug 40. Jacks 36, 38 are connected by means of plugs 42, 44, respectively. The remainder of FIG. 2 will be explained in conjunction with a circuit schematic shown in FIG. 3.

Figure 3:
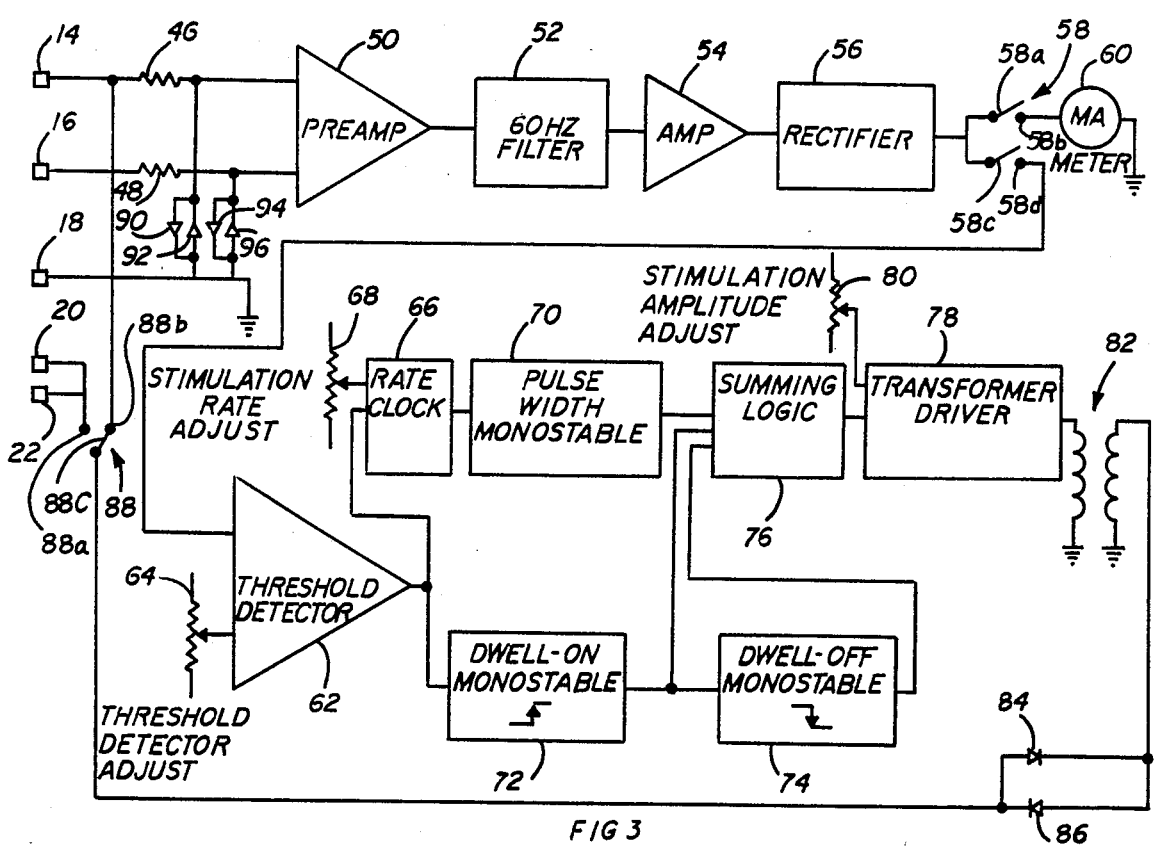
FIG. 3 is a simplified schematic drawing of the electrical circuitry of the present invention.

Turning now to FIG. 3, electrodes 14 through 22 are shown in conjunction with a simplified circuit diagram of control unit 11. An electromyographic (EMG) signal received by electrodes 14, 16 is transmitted through a pair of one meg-ohm resistors 46, 48, respectively, to a preamplifier 50 in control unit 11. Electrode 18 is connected to ground. Electrodes 14, 16, 18 are collectively referred to herein as signal reception electrode means.

The amplified EMG signal leaving amplifier 50 next passes through a 60-Hz. filter 52, another amplifier 54, and a rectifier 56.

A three-position function selector switch 58, also shown in FIG. 2, allows the patient or physical therapist to select one of three control unit functions: the operator may merely monitor the level of a patient initiated EMG signal, through a read out on a meter 60; the operator may select a function wherein control unit 11 operates as a transcutaneous electric nerve stimulator (TENS) through the production of an artificial stimulation signal; or the operator may both monitor the level of a patient-initiated EMG signal and at the same time produce an artificial stimulation signal.

With switch 58 adjusted to the EMG position designated for the switch in FIG. 2, contacts 58a, 58b in switch 58 close, whereby the output from rectifier 56 is feed solely to meter 60. With the switch adjusted to the EMG/TENS position designated in FIG. 2, contacts 58a, 58b close and contacts 58c, 58d close. With this position of the switch, the output from rectifier 56 is feed to meter 60 and in addition to circuitry producing an artificial stimulation signal through closed contacts 58c, 58d. With switch 58 adjusted to the TENS position designated in FIG. 2, the output from rectifier 56 is feed solely to the circuitry which produces an artificial stimulation signal.

With switch 58 moved to either the EMG/TENS or TENS positions (whereby to produce a stimulation signal), the amplified EMG signal leaving rectifier 56 is feed as input to a threshold detector 62. The threshold level of the detector is set by means of a threshold detector adjust 64. If a predetermined EMG threshold has been reached, the amplified EMG signal triggers threshold detector 62 and components of the unit are activated producing an artificial stimulation signal.

An EMG signal of sufficient intensity to trigger threshold detector 62 causes additional components of control unit 11, referred to herein as logic means, to function. A rate clock 66, which determines artificial stimulation signal frequency, is started. Rate clock 66 is adjustable by means of stimulation rate adjust 68. A pulse width monostable 70 controls the width of individual artificial stimulation signal pulses.

A dwell-on monostable 72 is triggered simultaneously with rate clock 66. When dwell-on monostable 72 times out, a dwell-off monostable 74 is triggered.

Inputs from the rate clock and pulse width monostable, dwell-on monostable and dwell-off monostable, referred to collectively herein as signal-producing means, are summed by a summing logic 76. When summing logic 76 receives a proper pattern of inputs, logic 76 generates a so-called logic means output, which triggers a transformer driver 78, which, through a stimulation amplitude adjust 80, controls the amplitude of a stimulation pulse, and which drives a step-up transformer 82. Driver 78 and transformer 82 comprise what is referred to herein as amplifier means.

Two transformer isolation diodes 84, 86 are placed in the circuit between transformer 82 and a stimulation select switch 88. Switch 88 enables the unit operator to select which of the two possible stimulation electrodes will receive an artificial stimulation signal. In reality, switch 88 is a part of miniature remote phone plug 44 (see FIG. 2), with the switch including two contacts, 88a, 88b, and a switch blade 88c which is normally spring biased to connect with contact 88b. When jack 38 is plugged into unit 11, blade 88c connects with contact 88a, artificial stimulation signals are transmitted to the remote stimulation electrodes. When plug 44 does not contain a jack, blade 88c connects with contact 88b, and an artificial stimulation signal is transmitted to the active electrode.

A typical EMG signal has a potential of 1–100-micro volts and a frequency in the 80–400-Hz. range. Control unit output is on the order of 20–80-volts with a frequency, set by rate adjust 68, of 40–120-Hz. An 80-Hz. frequency has been found experimentally to be most comfortable to a patient undergoing treatment. Additionally, the human skin has been found to have a resistance in the range of 1,000–3,000-ohms. It will be understood from what has above been explained that electrodes 14, 16, 18 must be capable of handling a very wide range of voltages.

Additionally, preamplifier 50 must be able to operate in the micro-volt range while being protected from voltages in the 20 to 80-volt range. The inclusion of resistors 46, 48, and input protection diodes 90, 92, 94, 96, prevents transformer output voltages from harming the preamplifier. Similarly, diodes 84, 86 prevent an EMG signal received by the electrodes from "seeing" the relatively low impedance of transformer 82—thereby properly directing the EMG signal into the preamplifier.

Assuming for a moment, that patient 12 is undergoing a re-education process of a debilitated muscle group in his left thigh, which still receives an EMG signal from his nervous system, patient 12 would probably be able to effect slight movement of his left leg. Surface electrodes would be attached as shown in FIG. 1, only on the patient's left leg. The remote electrodes would not be attached to the patient or the control unit. Unit 11 is turned on by means of a switch 98.

An EMG signal is detected across active electrode 14 and reference electrode 16. Ground electrode 18 enhances the performance of the system and provides a larger sensor area. Utilization of surface electrodes in pairs localizes detection of an EMG signal.

As previously stated, the EMG signal passes through preamplifier 50 and into filter 52. Filter 52 removes unwanted ambient electrical impulses, as might be input to the system if the patient is located near electrical equipment utilizing normal 110-volt 60-Hz. power.

Threshold detector 62 is adjustable by means of threshold detector adjust 64 to enable an EMG of a predetermined intensity to act as a trigger for the device. As previously stated, clock 66 and monostables 70, 72 and 74 provide input for summing logic 76 which generates an output that ultimately functions as an artificial stimulus to a muscle group.

It can be seen that without the inclusion of the aforementioned components, referred herein as signal producing means, the device could enter a perpetual state of oscillation. To prevent this from occuring, an EMG which exceeds the threshold value, as set by adjust 64, simutaneously triggers rate clock 66 and dwell-on monostable 72. Rate clock 66 will generally be set to an output frequency in the vicinity of 80-Hz. by stimulation rate adjust 68. Rate clock 66 and pulse width monostable 70 together determine the frequency of an amplified artificial stimulation signal. Dwell-on monostable 72 will time a first predetermined interval, as determined by a dwell-on time adjustment 100 (FIG. 2). Once the dwell-on monostable times out, the dwell-off monostable times a second predetermined interval, as set by a dwell-off time adjustment 102 (FIG. 2). The combination of the threshold detector and the dwell-on monostable comprises a means for controlling the so-called signal producing means. The dwell-off monostable essentially prevents successive patient-initiated EMG signals, or a signal generated by unit 11, from subsequently triggering the device within a predetermined time, and as such, is referred to herein as means preventing reinitiation of production of the stimulation signal.

As previously stated, the intensity or amplitude of the artificial stimulation signal may be varied between 20 and 80-volts, by stimulation amplitude adjust 80. A signal thus generated by transformer 82 is transmitted to the debilitated muscle group undergoing re-education through active electrode 14, which now acts as a stimulation electrode means, or a stimulation signal transmission means. In this situation, it can be said that the reception electrode and the stimulation electrode share a common housing. Although rather small sized electrodes would suffice to receive a patient-initiated electromyographic signal, a somewhat larger electrode is necessary as a stimulation electrode to prevent burning of the patient's skin where the electrode is applied.

Typical artificial stimulation signal strength is 20–80-volts, at 20–80-milliamperes and at a frequency of 40–120-Hz. A frequency of about 80-Hz. has been found to be most comfortable since it produces least amounts of cutaneous burning. A typical artificial stimulation signal will have a duration of 100–500-milliseconds as determined by the dwell-on monostable, followed by a system shutdown of 3–10-seconds, as determined by the dwell-off monostable.

Although the body is capable of initiating an EMG signal to a given muscle group approximately ten times per second, the transmission of an artificial stimulation signal at such a rate at an intensity required to re-educate a muscle group could easily result in burn damage to a patient's skin at the point of electrode contact. Further, such rapid stimulation would not result in the desired re-education of a debilitated muscle.

Returning momentarily to FIG. 1, should a patient need to re-educate a muscle group which is receiving an insufficient EMG signal, the muscle group can be re-educated by an artificially produced signal which is triggered by an EMG signal detected in a non-debilitated muscle group. In this instance, electrodes 14, 16, 18 would still detect an EMG signal in the patient's left leg, and, once remote leads 20, 22 were attached to jack 44, and remote electrodes 20, 22 applied to the patient's right leg, the signal generated in unit 11 would be transmitted to the extensor muscles of the patient's right leg. This positioning of electrodes would enable the patient to stimulate a debilitated muscle group in his right thigh by initiating an EMG signal in his left thigh. Obviously, the reception electrodes may be positioned adjacent any health muscle group. The reception electrode and stimulation electrode are independently housed in this situation.

Although a preferred embodiment of the device and the method of use has been set forth, it is appreciated that variations and modifications may be made without departing from the spirit of the invention.

It is claimed and desired to secure by Letters Patent:

1. A patient-initiated method of re-educating a debilitated muscle group including the brain control therefor, which muscle group is possessed by the patient, the method comprising repeatedly preforming the steps of
    (a) having the patient produce, through voluntary initiation of attempted movement in a limb consciously selected by the patient, an electromyographic signal in a muscle group that is responsible for limb movement,
    (b) detecting the electromyographic signal so produced when such has a predetermined intensity,
    (c) producing in response to said detected electromyographic signal a stimulation signal of greater intensity, and
    (d) essentially simultaneously with detection of the electromyographic signal transmitting the stimulation signal to a debilitated muscle group of the patient responsible for limb movement to produce response to the stimulation signal in the debilitated muscle group perceived by the patient to be response to the voluntarily initiated attempted movement of the limb, repeated perception by the patient of this response serving to re-educate the muscle group including the brain control therefor whereby the patient is enabled to produce limb movement without transmission of the stimulation signal.

2. The method of claim 1, wherein said stimulation signal is transmitted for a transmission time period of predetermined length, and on expiration of the transmission time period there is a shut-down period of non-transmission, said shut-down period having greater length than the length of the transmission period.

3. The method of claim 1, wherein the debilitated muscle group is responsible for limb movement in one limb of the patient, and the patient produced electromyographic signal is produced in a muscle group that is responsible for movement in the same limb.

4. The method of claim 1, wherein the debilitated muscle group is responsible for limb movement in one limb of the patient and the patient produced electromyographic signal is produced in a musele group that is responsible for movement in a symmetric limb on the opposite side of the patient from said one limb.

* * * * *